(12) United States Patent
Jeon et al.

(10) Patent No.: US 9,506,808 B2
(45) Date of Patent: Nov. 29, 2016

(54) HANDPIECE WITH INTEGRATED OPTICAL SYSTEM FOR PHOTOTHERMAL RADIOMETRY AND LUMINESCENCE MEASUREMENTS

(75) Inventors: Jin-Seok Jeon, Windsor (CA); Andreas Mandelis, Scarborough (CA); Stephen Abrams, Toronto (CA); Anna Matvienko, Toronto (CA); Koneswaran Sivagurunathan, Scarborough (CA); Josh Silvertown, Toronto (CA); Adam Hellen, Richmond Hill (CA)

(73) Assignee: QUANTUM DENTAL TECHNOLOGIES, INC., Toronto, ON (CA)

( * ) Notice: Subject to any disclaimer, the term of this patent is extended or adjusted under 35 U.S.C. 154(b) by 546 days.

(21) Appl. No.: 13/697,747

(22) PCT Filed: May 13, 2011

(86) PCT No.: PCT/CA2011/050303
§ 371 (c)(1),
(2), (4) Date: Feb. 25, 2013

(87) PCT Pub. No.: WO2011/140664
PCT Pub. Date: Nov. 17, 2011

(65) Prior Publication Data
US 2013/0141558 A1 Jun. 6, 2013

Related U.S. Application Data

(60) Provisional application No. 61/334,436, filed on May 13, 2010.

(51) Int. Cl.
*G01J 5/04* (2006.01)
*A61B 6/14* (2006.01)
(Continued)

(52) U.S. Cl.
CPC ............. *G01J 5/10* (2013.01); *A61B 1/00177* (2013.01); *A61B 1/24* (2013.01); *A61B 5/0088* (2013.01);
(Continued)

(58) Field of Classification Search
CPC .......................... A61B 2018/202; G01J 5/048
USPC ........................................................... 348/77
See application file for complete search history.

(56) References Cited

U.S. PATENT DOCUMENTS 5,371,368 A 12/1994 Alfano et al.
5,880,826 A 3/1999 Jung et al.
(Continued)

FOREIGN PATENT DOCUMENTS

CA 2691558 9/2008
JP 2001-321388 11/2001
(Continued)

OTHER PUBLICATIONS

Jeon et al. "Depth profilometric case studies in caries diagnostics of human teeth using modulated laser radiometry and luminescence.", Review of Scientific Instruments, vol. 74, No. 1, Jan. 2003, pp. 380-383.

(Continued)

*Primary Examiner* — Mikhail Itskovich
(74) *Attorney, Agent, or Firm* — Lynn C. Schumacher; Stephen W. Leonard; Hill & Schumacher

(57) ABSTRACT

An apparatus is provided for performing photothermal measurements on a object. The apparatus, which may be provided as a handpiece, houses optical components including a laser, an infrared detector, a dichroic beamsplitter, and focusing and beam directing optics for the delivery of a laser beam to, and the collection of photothermal radiation from, a measured object. Some of the optical components may be provided on an optical bench that is directly attached to a thermally conductive tip portion for the passive heat sinking of internal optical components. The apparatus may further include a sampling optical element and a photodetector for the detection of luminescence, and a camera for obtaining an image of the object during a diagnostic procedure. The apparatus may be employed for the scanning of a tooth to determine an oral health status of the tooth.

32 Claims, 10 Drawing Sheets

(51) Int. Cl.

| | | |
|---|---|---|
| *G01N 21/63* | (2006.01) | |
| *A61B 18/20* | (2006.01) | |
| *G01J 5/10* | (2006.01) | |
| *A61B 1/00* | (2006.01) | |
| *A61B 1/24* | (2006.01) | |
| *A61B 5/00* | (2006.01) | |
| *G01J 1/02* | (2006.01) | |
| *G01J 1/58* | (2006.01) | |
| *G01J 3/02* | (2006.01) | |
| *H04N 7/18* | (2006.01) | |
| *A61B 1/05* | (2006.01) | |

(52) U.S. Cl.
CPC .............. *A61B 5/0093* (2013.01); *A61B 6/14* (2013.01); *G01J 1/0233* (2013.01); *G01J 1/58* (2013.01); *G01J 3/0272* (2013.01); *G01J 5/048* (2013.01); *G01N 21/63* (2013.01); *H04N 7/18* (2013.01); *A61B 1/05* (2013.01); *A61B 2018/202* (2013.01); *A61B 2560/0233* (2013.01)

(56) References Cited

U.S. PATENT DOCUMENTS

| | | | |
|---|---|---|---|
| 6,459,484 | B1 * | 10/2002 | Yokoi ............................ 356/318 |
| 6,584,341 | B1 | 6/2003 | Mandelis et al. |
| 7,148,970 | B2 | 12/2006 | de Boer |
| 7,525,661 | B2 | 4/2009 | Mandelis et al. |
| 7,729,734 | B2 | 6/2010 | Mandelis et al. |
| 8,306,608 | B2 | 11/2012 | Mandelis et al. |
| 8,556,625 | B2 | 10/2013 | Lovely |
| 2002/0115908 | A1 * | 8/2002 | Farkas et al. ................... 600/178 |
| 2004/0059282 | A1 | 3/2004 | Flock et al. |
| 2004/0236269 | A1 | 11/2004 | Marchitto et al. |
| 2006/0052661 | A1 * | 3/2006 | Gannot et al. ................. 600/108 |
| 2006/0184040 | A1 | 8/2006 | Keller et al. |
| 2007/0093797 | A1 | 4/2007 | Chan et al. |
| 2010/0049180 | A1 | 2/2010 | Wells et al. |
| 2011/0040358 | A1 * | 2/2011 | Bean et al. ........................ 607/89 |
| 2011/0118571 | A1 | 5/2011 | Mandelis et al. |

FOREIGN PATENT DOCUMENTS

| | | |
|---|---|---|
| JP | 2004-230122 | 8/2004 |
| JP | 2006341025 | 12/2006 |
| JP | 2007537802 | 12/2007 |
| JP | 2008-192215 | 8/2008 |
| JP | 2009183323 | 8/2009 |
| WO | 2005110206 | 11/2005 |
| WO | 2006072176 A1 | 7/2006 |

OTHER PUBLICATIONS

Jeon et al. "Diagnosis of Pit and Fissure Caries using Frequency-Domain Infrared Photothermal Radiometry and Modulated Laser Luminescence." Caries Research, vol. 38, No. 6, Nov. 2004, pp. 497-513.

Kromer, Phillip. "UTILIA: A PC-Based Lock in Amplifier." Aug. 3, 2002.

Nicolaides et al., "Quantitative dental measurements by use of simultaneous frequency-domain laser infrared photothermal radiometry and luminescence." Applied Optics, vol. 41, No. 4, Feb. 1, 2002, pp. 768-777.

Wei et al., "Integrated Optical Elliptic Couplers: Modeling, Design, and Applications." Journal of Lightwave Tech, vol. 15, No. 5, May 1997, pp. 906-912.

Jeon et al., "Nonintrusive, noncontacting frequency-domain photothermal radiometry and luminiscence depth profilometry of carious and artificial subsurface lesions in human teeth", Journal of Biomedical Optics, vol. 9, No. 4, Jul./Aug. 2004. (R.J. Jeon, A Mandelis, V. Sanchez). *Section 2.2, p. 806.

Nicolaides et al., "Novel dental dynamic depth profilometric imaging using simultaneous frequency-domain infrared photothermal radiometry and laser luminescence", Journal of Biomedical Optics, vol. 5, No. 1, Jan. 2000, pp. 31-39 (L.Nicolaides and A. Mandelis) *section 2.2, Fig. 1.

International Search Report (PCT/CA2011/050303) dated Sep. 14, 2011.

* cited by examiner

HANDPIECE WITH INTEGRATED OPTICAL SYSTEM FOR PHOTOTHERMAL RADIOMETRY AND LUMINESCENCE MEASUREMENTS

CROSS-REFERENCE TO RELATED APPLICATION

This application is a National Phase application claiming the benefit of No. PCT/CA2011/050303 filed on May 13, 2011, in English, which further claims priority to U.S. Provisional Application No. 61/334,436 titled "Handpiece with Integrated Optical System for Photothermal Radiometry and Luminescence Measurements" and filed on May 13, 2010, the entire contents of which are incorporated herein by reference.

BACKGROUND

The present disclosure relates to detection methods in oral health care.

With the widespread use of fluoride, the prevalence of dental caries has been considerably reduced. Nonetheless, the development of a non-invasive, non-contact technique that can detect and monitor early demineralization or small carious lesions on or beneath the enamel, dentin, root surface or around the margins of dental restorations, is essential for the clinical management of this problem.

In dentistry, the aim of recent scientific research has been the use of laser fluorescence for detection of tooth demineralization and dental caries (e.g. enamel and/or root), dental deposits, and dental calculus and quantitative analysis of lesion depth and size, as well as the mineral composition of the enamel [M. L. Sinyaeva, Ad. A. Mamedov, S. Yu. Vasilchenko, A. I. Volkova, and V. B. Loschenov, 2003, "Fluorescence Diagnostics in Dentistry", Laser Physics, 14, No. 8, 2004, pp. 1132-1140]. These principles have been used to develop a number of fluorescence-based technologies, such as QLF™ and DIAGNOdent™ diagnostic devices.

UV radiation (488 nm) has been used to examine dental enamel [Susan M. Higham, Neil Pender, Elbert de Josselin de Jong, and Philip W. Smith, 2009. Journal of Applied Physics 105, 102048, R. Hibst and R. Paulus, Proc. SPIE 3593, 141 (1999)]. The studies showed that autofluorescence of healthy enamel were peaked at a wavelength of 533 nm, whereas the autofluorescence of carious tissue was red-shifted by 40 nm. It was also demonstrated that the autofluorescence intensity of carious zones was an order-of-magnitude lower than the autofluorescence intensity of a healthy tooth in spite of the fact that the absorbance of the carious zone at the excitation wavelength was significantly higher.

The reduction in fluorescence when enamel demineralizes or a carious lesion has developed has been attributed to the increase in porosity of carious lesions when compared with sound enamel. There is an associated uptake of water and decrease in the refractive index of the lesion resulting in increased scattering and a decrease in light-path length, absorption, and autofluorescence [H. Bjelkhagan, F. Sundström, B. Angmar-Månsson, and H. Ryder, Swed Dent. J. 6, 1982].

At long excitation wavelengths, the autofluorescence intensity of a carious cavity can be higher than the autofluorescence intensity of healthy tissue [R. Hibst et al.]. For excitation wavelengths of 640 or 655 nm, the integral (at wavelengths greater than 680 nm) autofluorescence intensity of a carious lesion could be approximately one order-of-magnitude greater than the corresponding integral autofluorescence intensity of healthy enamel. There is some indication that the induced fluorescence with these wavelengths results from the excitation of fluorescent fluorophores from bacterial metabolites. These fluorophores are thought to originate from porphyrins found in some bacterial species [S. M. Higham et al.].

More recently, a new system has been developed based on the combination of laser induced fluorescence and photothermal radiometry. The system, commercially available as The Canary Dental Caries Detection System™, which examines luminescence and photothermal effect (PTR-LUM) of laser light on a tooth, as described in US Patent Application No. 2007/0021670, titled "Method and Apparatus Using Infrared Photothermal Radiometry (PTR) and Modulated Laser Luminescence (LUM) for Diagnostics of Defects in Teeth", filed Jul. 18, 2006. The laser is non-invasive and can detect tooth decay a fraction of a millimeter in size and up to five millimeters below a tooth's surface. When pulses of laser light are focused on a tooth, the tooth glows and releases heat. By analyzing the emitted light and heat signatures from the tooth, very accurate information about the tooth's condition can be obtained including signs of early demineralization (lesions) of enamel [Nicolaides, L, Mandelis, A., Abrams, S. H., "Novel Dental Dynamic Depth Profilometric Imaging using Simultaneous Frequency Domain Infrared Photothermal Radiometry and Laser Luminescence", Journal of Biomedical Optics, 2000, January, Volume 5, #1, pages 31-39, Jeon, R. J., Han, C., Mandelis, A., Sanchez, V Abrams, S. H "Non-intrusive, Non-contacting Frequency-Domain Photothermal Radiometry and Luminescence Depth Profilometry of Carious and Artificial Sub-surface Lesions in Human Teeth," Journal of Biomedical Optics 2004, July-August, 9, #4, 809-81, Jeon R. J., Hellen A Matvienko A Mandelis A Abrams S. H Amaechi B. T., In vitro Detection and Quantification of Enamel and Root Caries Using Infrared Photothermal Radiometry and Modulated Luminescence. Journal of Biomedical Optics 13(3), 048803, 2008]. As a lesion grows, there is a corresponding change in the signal. As remineralization progresses, a signal reversal indicates an improvement in the condition of the tooth. By changing the frequency of the signal one can probe up to 5 mm below the tooth surface. Low frequency signals can penetrate the defects and lesions beneath the tooth surface.

One significant drawback with the aforementioned systems is the complex and expensive optical delivery systems that are typically needed. Moreover, some systems involve a handpiece that is optically coupled to a remote detector and laser source unit via an expensive fiber bundle assembly. This results in numerous drawbacks, including cost, complexity, and inconvenience of use due to the weight of the cables sheathing the fiber bundles.

SUMMARY

An apparatus is provided for performing photothermal measurements on a sample, such as a surface of a tooth. The apparatus, which may be provided in the form of a handpiece, houses optical components including a laser, an infrared detector, a dichroic beamsplitter, and focusing and beam directing optics for the delivery of a laser beam to, and the collection of photothermal radiation from, the measured sample. Some of the optical components may be provided on an optical bench that is directly attached to a thermally conductive tip portion for the passive heat sinking of internal optical components. The handpiece may include a beam sampling optical element and a photodetector for the detection of luminescence, and a camera for obtaining an image of a sample during a measurement.

Accordingly, in one aspect, there is provided an apparatus for detecting photothermal radiation from an object, the apparatus comprising: an elongate housing; a laser for producing a laser beam within the housing; a focusing element positioned to focus the laser beam through an aperture at a distal portion of the housing and onto a surface of the object, and to collect photothermal radiation generated within the object in response to the laser beam; and a dichroic beamsplitter positioned within the housing to spatially separate the photothermal radiation from the laser beam; and an infrared detector provided within the housing for detecting the photothermal radiation.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

In a one embodiment, a handpiece for photothermal radiometric (PTR) and luminescence (LUM) diagnostic measurements is provided in which optical components are integrated onto an optical bench. As discussed below, by integrating optical components directly into the handpiece onto an optical bench, a compact, robust and inexpensive handpiece is provided that is well suited to routine clinical use.

Figure 1:
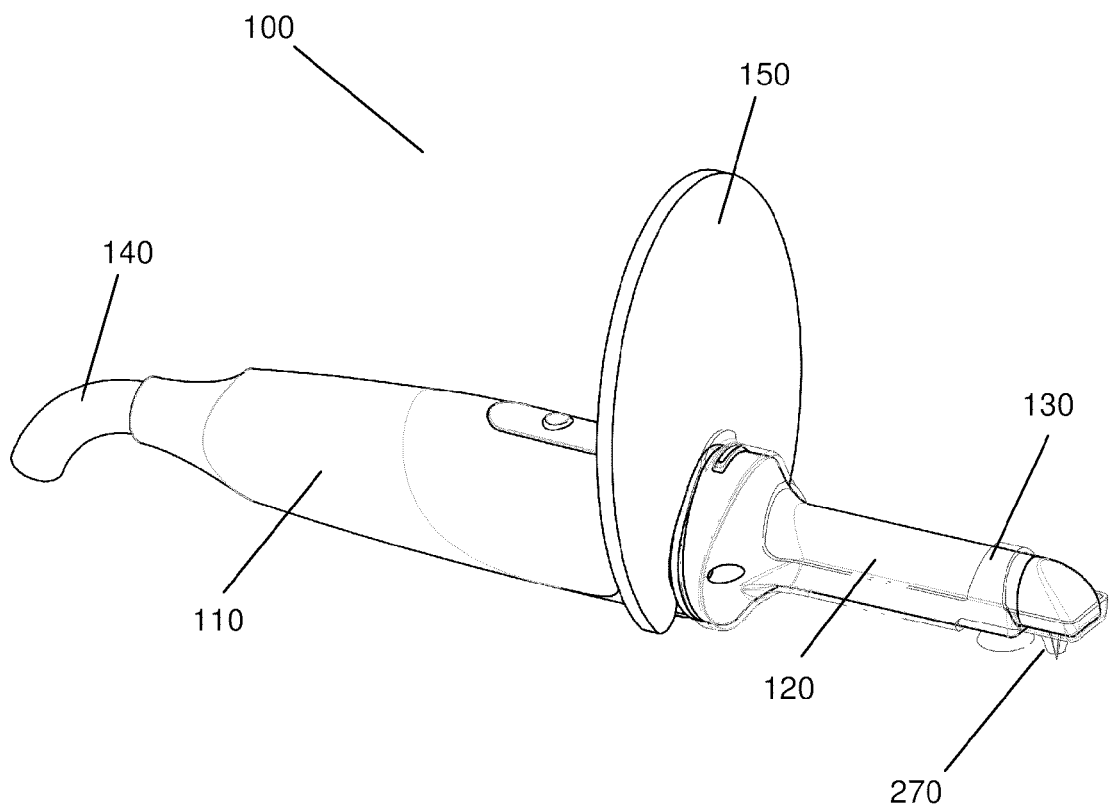
FIG. 1 provides an isometric view of an oral health diagnostic handpiece for use in photothermal radiometric (PTR) and luminescence (LUM) measurement of a tooth surface.
Figure 2:
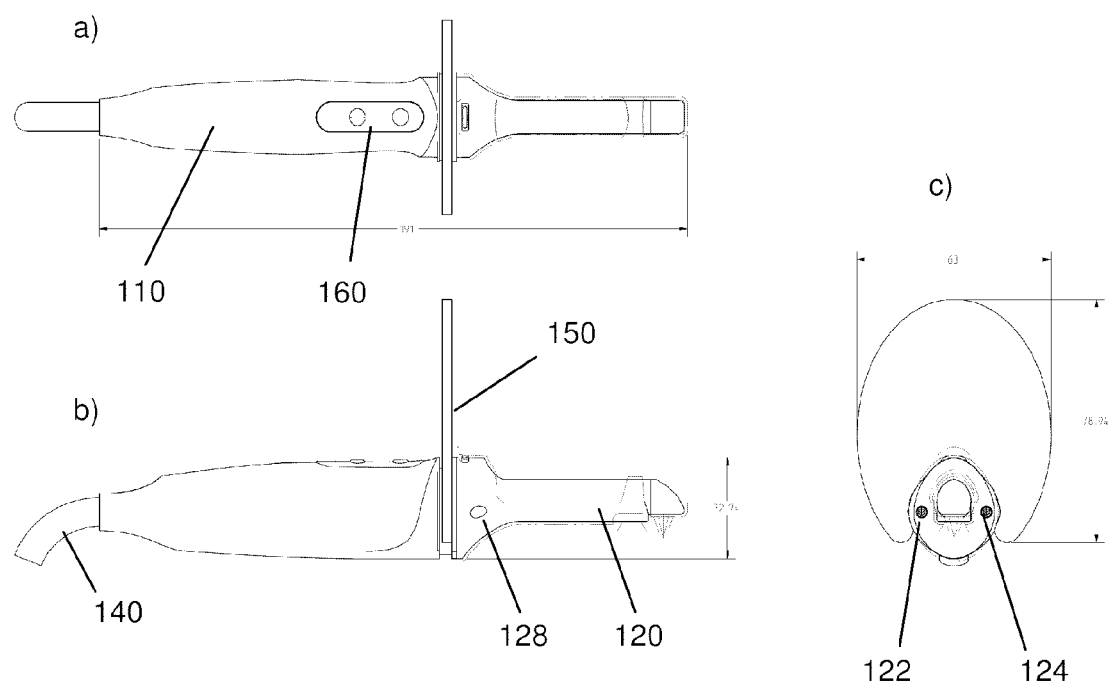
FIG. 2 provides (a) plan, (b) side and (c) lateral views of the oral health diagnostic handpiece shown in FIG. 1.

FIG. 1 illustrates an example implementation of a PTR-LUM handpiece 100, as shown in an external isometric view, and FIG. 2 provides edge, side and plan views of the handpiece. Handpiece 100 includes a body portion 110 and a tip portion 120. Tip portion 120 is secured to the body portion at a proximal end of tip portion 120, and delivers and receives optical radiation at distal end. Tip portion 120 slidably receives protective shell 130, which is removably attached along an axial direction of tip portion. Optical components, including optical sources and detectors, are mounted on an optical bench housed within handpiece 100, as further discussed below. Handpiece 100 is connected to an external control and processing apparatus (not shown) through electrical cable 140.

An optical filter 150 is optionally provided to block scattered laser radiation and to protect operator's eyes. The filter may be snap-fit into a receiving slot for easy attachment and removal. By incorporating the optical filter directly onto the handpiece, a clinician need not wear protective laser goggles throughout a scanning or diagnostic procedure, and may easily view a patient's oral anatomy by moving the handpiece to remove the filter from a direct line of sight. This feature is clinically useful because it is often important for a clinician to view the oral anatomy in true colour to aid in a diagnosis or guide a diagnostic procedure.

Referring to FIG. 2, handpiece 100 may be employed to communicate with control and processing unit (described further below) using buttons 160 located on the top of body portion 110. For example, a user may press a button to initiate and/or terminate a measurement or series of measurements. Buttons 160, or other input and/or control elements, may be fitted into handpiece 100 such that a fluid tight seal is provided, preventing the leakage of fluids into the interior of the handpiece.

As shown in FIG. 2, tip portion 120 may be secured to body portion 110 by fasteners 122 and 124 that are received in slots 128 provided in tip portion (only a single slot is shown in FIG. 2) and mate with a threaded bore in body portion. Accordingly, the tip portion needs not to be secured to the body portion through the internal optical bench, as shown further below. An internal o-ring may be employed to provide a seal between body portion 110 and tip portion 120.

The example handpiece provides a lightweight an ergonomic design that is convenient and well adapted for clinical use. By housing all optical components, (for example, a laser diode and detectors) within the body and tip portions of the handpiece, the need to optical deliver radiation to and from the handpiece via optical fiber bundles is removed, thus allowing for the device to be connected to the control and processing apparatus via a simple, flexible, inexpensive and lightweight electrical cable (the cable may house multiple electrical wires for carrying various control and detected signals and power). Furthermore, the use of an electrical cable as opposed to an optical cable decreases the minimum cable bend radius, allowing for the handpiece to be manipulated in a wider range of motions and directions during a clinical procedure. Shielding may be placed over the cable to minimize electrical interference with the signal as it transits the cable.

In one embodiment, handpiece 100 has a size that is sufficiently small to allow for scanning teeth within the mouth of a child or an adult. Furthermore, the handpiece design protects the optical elements from damage during normal use. As shown in FIG. 2, the tip piece 120 may be removed from the body piece 110 using fasteners 122 and 124, which enable the efficient manufacturing and field repair.

Figure 3:
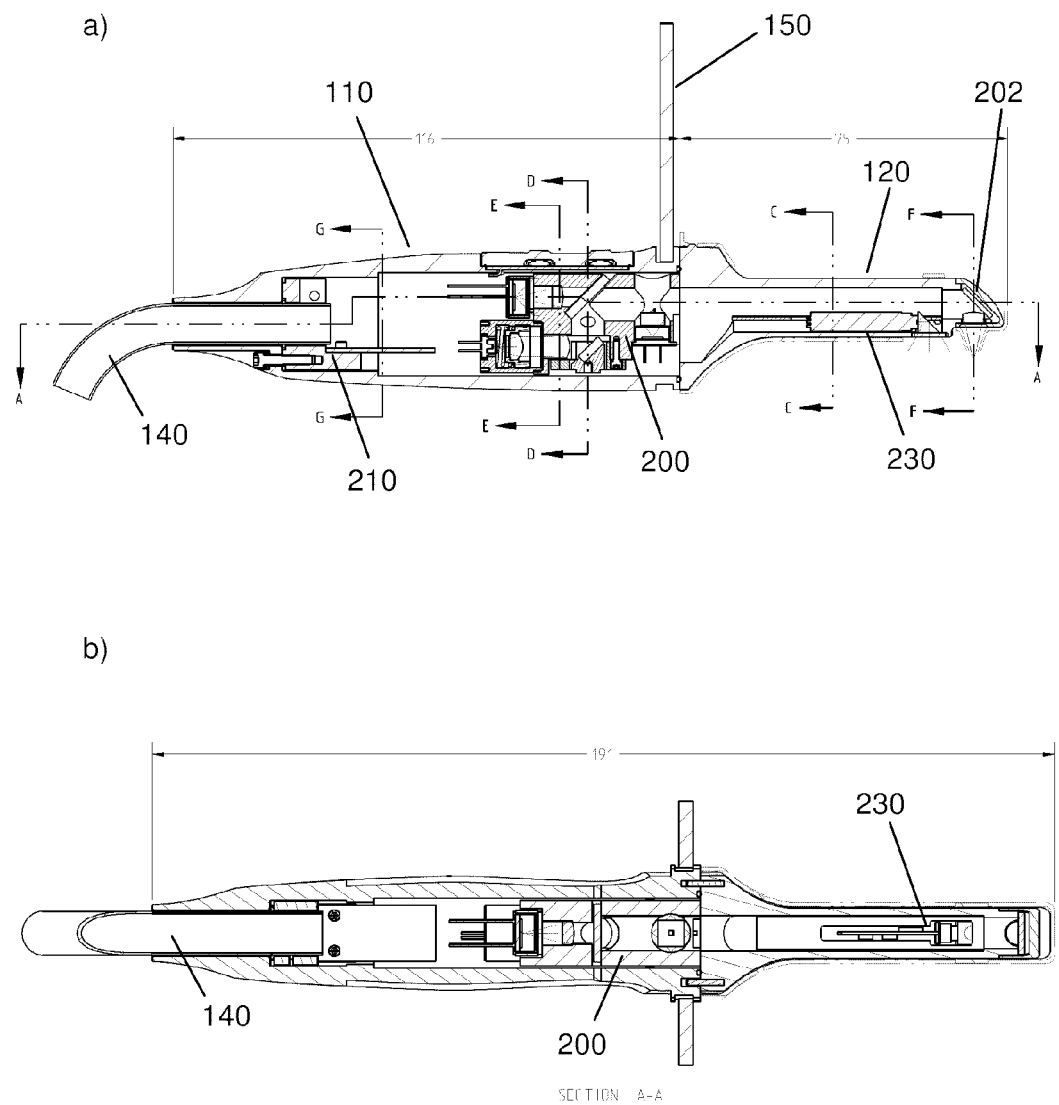
FIGS. 3(a) and (b) provide cross-sectional views of the oral health diagnostic handpiece shown in FIG. 1.

FIG. 3 provides a detailed view of the internal components housed within body portion 110 and tip portion 120. Optical bench 200 is contained within body portion 110, which also receives electrical cable 140 in strain relief apparatus 210 (additional wires, and electrical connections to the optical components, are not shown). Electrical cable 140 electrically interfaces the detector and laser with an external control and processing apparatus for providing power to the laser and for processing signals from the detectors. Optical bench 200 has attached thereto a number of optical components that will be described further below. Tip portion 120 includes beam focusing, and optional beam directing, optical components 202 at its distal end and also houses optional camera 230 for obtaining an image of a tooth during a diagnostic procedure.

Figure 4:
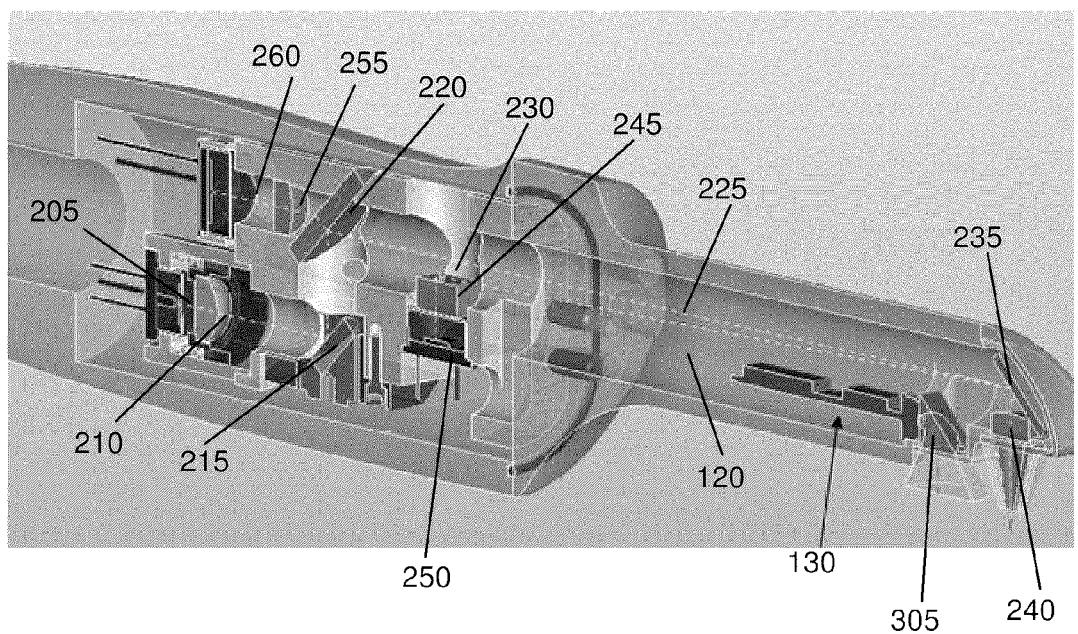
FIG. 4 is a cross-sectional view of the oral health diagnostic handpiece in which the optical bench is shown in detail.

A detailed view of the folded optical apparatus contained within the body portion 110 and tip portion 120 is shown in FIG. 4. Optical bench 200 supports semiconductor laser 205 and lens 210, which collimates emitted laser light that is subsequently redirected by a mirror 215 towards dichroic beamsplitter 220. Semiconductor laser 205 may be a laser diode having a wavelength of approximately 660 nm for the simultaneous generation of luminescence and photothermal radiation from a tooth surface.

The collimated laser beam is redirected by dichroic beamsplitter 220, which has provided thereon an optical coating having high reflectivity at the wavelength of the incident laser beam while passing thermal radiation. The laser beam propagates in a substantially axial direction into tip portion 120 along beam path 225, bypassing pick-off prism 230 and encountering mirror 235 at the distal end of tip portion 120. Mirror 235 reflects the collimated laser beam towards focusing element 240, which focuses the laser beam as it emerges from tip portion 120. It is to be understood that the laser beam need not exit the device in a direction perpendicular to its internal propagation axis.

Focusing element 240 is optically transmissive to light at the laser wavelength and at the wavelength of luminescent and photothermal radiation. In one example, the focusing element is transmissive in the visible spectrum and in the mid-infrared spectrum. Focusing element 240 has a focal length suitable for focusing the laser to a desired spot size. For example, a focal length of 8.6 mm produces a spot size of approximately 50 micrometers on average. Focusing element 240 provides the additional role of collecting and substantially collimating both luminescent and photothermal radiation emitted from a tooth surface in response to laser irradiation. While focusing element 240 is shown as a transmissive optical component, it will be apparent to those skilled in the art that focusing element 240 and mirror 235 could be replaced with a single curved mirror, such as an off-axis parabolic mirror.

Collected luminescence is directed by mirror 235 along an axis of tip portion 120, and a portion of the collected luminescence beam encounters a beam sampling element such as pickoff prism 230 (or another suitable element, such as a filter) and is directed towards optical filter 245 and photodetector 250. Optical filter 245 removes unwanted reflected and scattered laser light, and photodetector 250 is selected to have a spectral response suitable for the detection of the collected luminescence. In one example, photodetector 250 may be a silicon photodiode, and optical filter 245 may be an inexpensive color glass filter having a bandwidth and optical density matched to the laser wavelength and power (such as RG 715 Longpass color filter).

As noted above, focusing element 240 also collects and collimates emitted photothermal radiation, which is reflected by mirror 235 and directed towards dichroic beamsplitter 220. Dichroic beamsplitter 220 passes infrared radiation and reflects a substantial portion of scattered laser light. The dichroic beamsplitter 220 may also substantially reflect collected luminescence.

In one embodiment, an optical absorbing element, such as an absorbing window, may be placed between dichroic beamsplitter 220 and infrared detector 260 for attenuating both collected luminescence and scattered and/or residual laser light and transmitting photothermal radiation in the mid-infrared spectral region. In one example, the dichroic beamsplitter may further incorporate an absorptive substrate. A suitable material for the absorptive substrate is a long pass filtering material, such as germanium, which absorbs light having a wavelength less than approximately 1.85 microns.

In another example embodiment, the positions of infrared detector 260 and laser 205 may be reversed, and dichroic beamsplitter 220 may have an optical coating for transmitting the laser beam and luminescence radiation, and reflecting the photothermal radiation. In such an embodiment, it is beneficial to include the absorptive window described above to attenuate reflected laser power and luminescence radiation that would be otherwise detected by infrared detector 260.

Dichroic beamsplitter transmits collected photothermal radiation, which is subsequently focused by lens 255 onto infrared detector 260. Infrared detector may be a sensitive mid-infrared detector, such as a photovoltaic HgCdZnTe detector, with a sensitive spectral region spanning approximately 2 to 5 µm. Infrared detector 260 may be mounted on a thermo-electric cooler for enhanced performance and sensitivity.

As shown in FIG. 4, the optical components described above (with the exception of the optical components provided in tip portion 120) are mounted on optical bench 200. In one example implementation, optical bench 200 is formed in a lightweight and thermally conductive material, such as aluminum.

In the example implementation shown in the FIG. 4, optical bench, while housed within body portion 110, is attached to tip portion 120, thereby enabling rapid and efficient heat sinking into tip portion 120. Accordingly, tip portion 120 may also be made from a lightweight and thermally conductive material, such as aluminum. Such an embodiment enables tip portion to act as an efficient air-cooled heat sink for optical components (primarily the laser diode and optionally a thermo-electric (TE) cooler attached to detector 260) mounted on optical bench 200. This feature is especially useful for improving the performance of thermal detector 260, which may have a noise floor that is strongly dependent on temperature (such as in the case of the example HgCdZnTe detector described above). Furthermore, by attaching the optical bench directly to the rigid tip portion 120, improved mechanical isolation may be obtained relative to attaching the optical components to the body portion 110.

Figure 5:
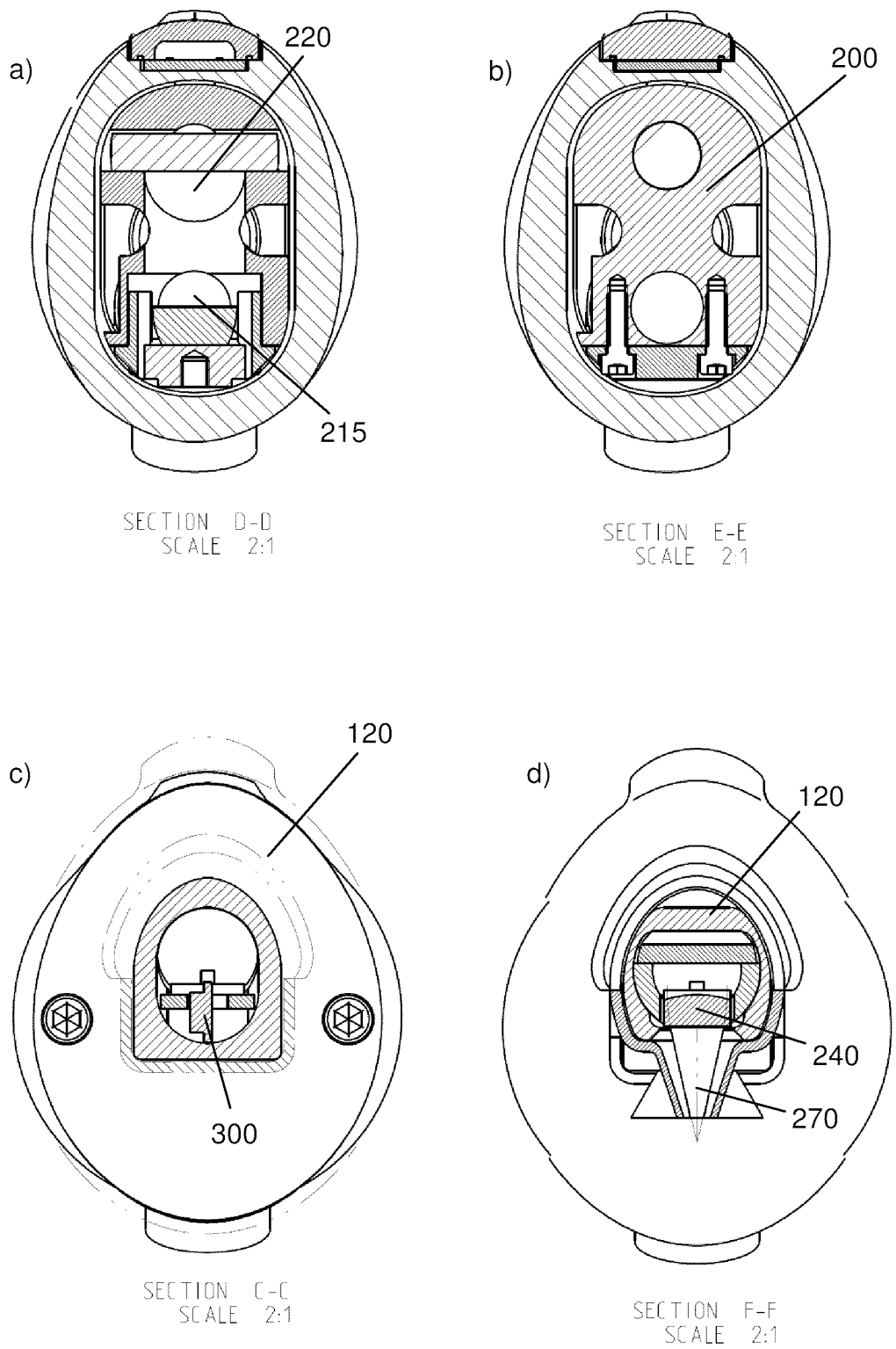
FIGS. 5(a)-(d) shown various cross-sectional views of the oral health diagnostic handpiece shown in FIG. 1, where the views are shown in a plane perpendicular to the longitudinal axis of the handpiece.

FIG. 5 provides a series of section views, where each view is in a plane perpendicular to the longitudinal axis of the handpiece. FIG. 5(a) shows a section through dichroic beamsplitter 220 and reflective folding mirror 215, while FIG. 5(b) illustrates a section through the optical bench 200 behind the dichroic beamsplitter 220 and reflective mirror 215. FIG. 5(c) illustrates a cross section through camera 300 (discussed further below) and FIG. 5(d) shows a cross section through the collection optics located at the distal end of tip portion 120, including focusing element 240. FIG. 5(d) also shows a cone 270 illustrating the beam shape of the laser, and a cross section through protective shell 130 (described further below).

In order to obtain sensitive detection of the laser-induced photothermal radiation and luminescence, the handpiece may interface with a phase-sensitive detection system such as a lock-in amplifier. In such an embodiment, the laser intensity is modulated at a desired frequency and both the detector signal and a reference signal related to the phase of the modulated laser current is provided to the lock-in amplifier. It will be apparent to those skilled in the art that other modulation methods may be used. For example, in one embodiment, the laser power beam may be optically chopped via a mechanical chopping wheel integrated into the handpiece, where the chopping wheel would provide additional active cooling of the detector via forced air convection. The lock-in amplifier may be provided on a data acquisition board housed within the control and processing unit. A suitable data acquisition board for providing lock-in functionality is the National Instruments NI USB-6221-OEM board. Alternatively, the lock-in amplified may be provided separately in an additional system that is interfaced to the control and processing unit.

Figure 6A:
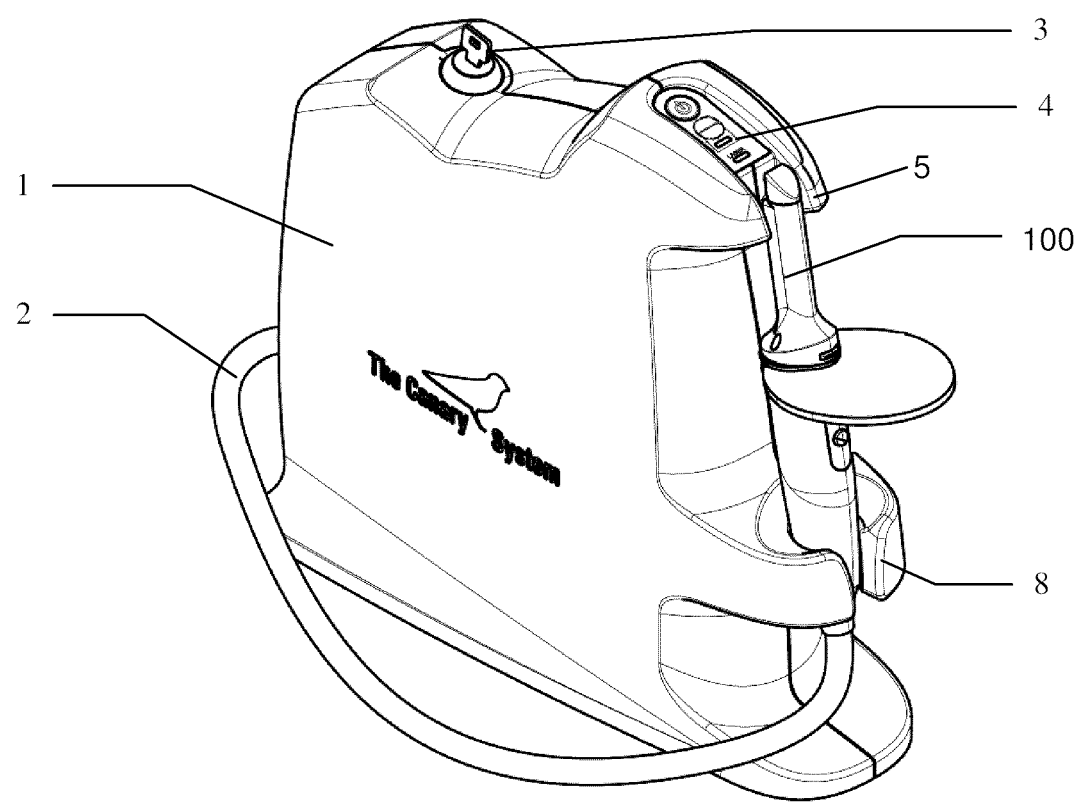
FIG. 6(a) shows an embodiment of a control and processing unit for use with the handpiece.
Figure 6B:
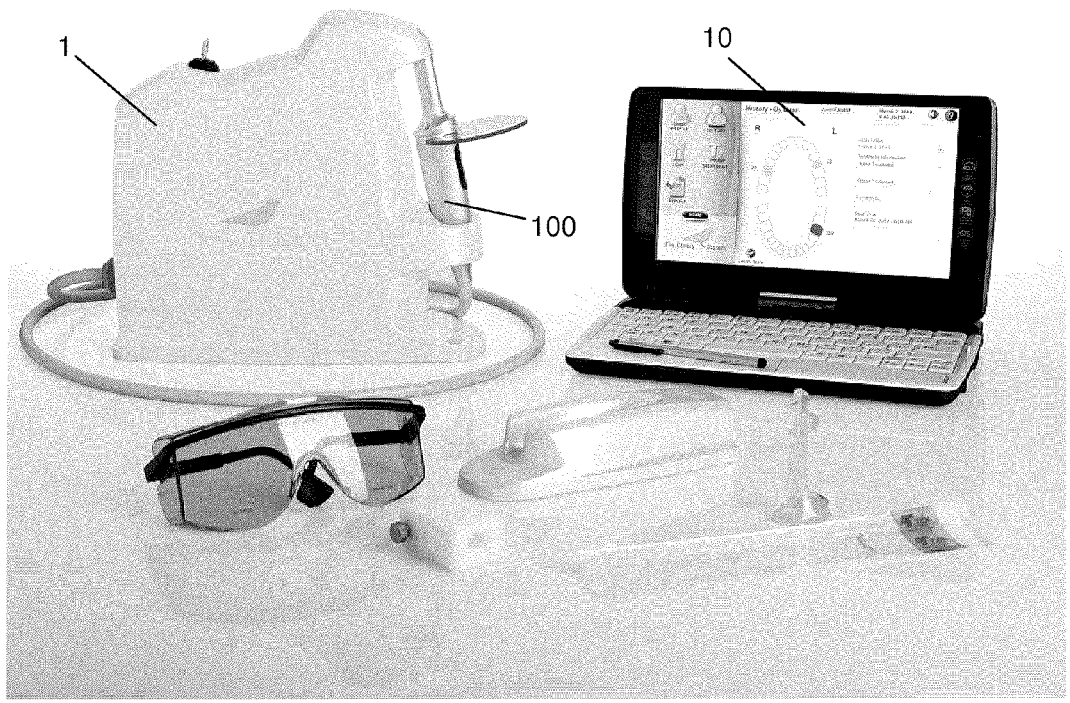
FIG. 6(b) shows a photograph of the handpiece, control and processing unit, and other system accessories.

FIG. 6(a) illustrates an example implementation of a control and processing unit 1 that contains the data acquisition board and additional electronics required for processing, user interfacing, and optional external networking. Control and processing unit 1 may include a processor, a memory, a data bus, and may include storage media, such as flash memory or a hard disk. Control and processing unit 1 is shown interfaced to handpiece 100 through cable 2. Handpiece 100 is supported at handpiece support structure 8, which is shaped to secure handpiece 100 when not in use, and a recess 5 to protect the distal end of tip portion 120 when handpiece 100 is secured. Control and processing unit may also include operation key 3 and external controls 4. FIG. 6(b) shows a photograph of control and processing unit 1, handpiece 100, and an external computing device 10, among additional accessories for use with the system.

Control and processing unit 1 may be programmed to process diagnostic measurements obtained from handpiece 100. For example, control and processing unit 1 may perform many functions, including, but not limited to, generating a numerical output associated with the tooth surface or section of tooth surface examined based on the measured signals, storing and/or processing diagnostic data, storing and/or processing image data, display images, signals or numerical output, and storing information relating to treatment recommendations and patient information.

In one embodiment, control and processing unit 1 processes received photothermal (PTR) and luminescence (LUM) measurements to provide a composite numerical result that is correlated with an oral health status of a scanned tooth. In an embodiment providing a single unified quantitative indication of oral health from a measurement at a given location, the data from a given measurement is stored by control and processing unit 1 as four separate signals; PTR amplitude and phase and LUM amplitude and phase. A unified diagnostic measure may be obtained by combining the four measured signals. In one example implementation, the signals are processed according to the following weighting formula:

PTR Amplitude weighted at 45% of the total value
PTR Phase weighted at 15% of the total value
LUM Phase weighted at 10% of the total value
LUM Amplitude weighted at 30% of the total value The four readings may be compared to the readings one finds from the healthy enamel surface and/or from a standardized piece of hydroxyapatite. The measured signal may additionally or alternatively be compared to healthy enamel surface. Results from the comparison step may be provided on a fixed scale for each reading, for example, on a scale of 1 to 100 (the scales need not be equal for each reading type), indicating a severity of a condition. The four fixed-scale results may then be weighted as described above, providing the operator a ranking or range (for example, on a scale from 1-100) indicating the health of the area examined.

In another example embodiment, the reading from a single frequency may be combined in the following manner:

$$(PTR\ amplitude \times PTR\ Phase)/(LUM\ Amplitude \times LUM\ Phase),$$

to create one single reading.

Error checking may be performed by combining the standard deviation from each reading into one number as follows:

$$LUM\ amplitude \times LUM\ Phase \times PTR\ Amplitude \times PTR\ Phase.$$

The ratio of single reading/combined standard deviation may then be examined, and if the ratio increases dramatically, this can be indicative of an error in the reading, which may then be conveyed to the operator. The single reading may be conveyed to the operator along with its difference from the single reading derived from examining health enamel and healthy teeth.

In another example, error checking may be performed by combining the standard deviation from each reading into one number as follows:

$$100 \times \{(PTR\text{-}A\text{-}std/PTR\text{-}A)^2 + (PTR\text{-}P\text{-}std/PTR\text{-}P)^2 + (LUM\text{-}A\text{-}std/LUM\text{-}A)^2 + (LUM\text{-}P\text{-}std/LUM\text{-}P)^2\}^{1/2}$$

In another embodiment, a camera is further provided in the handpiece for obtaining an image of a selected tooth. In an example configuration shown in FIG. 4, camera 300 is located near the distal end of tip portion 120. Locating the camera near the distal end of the tip portion provides numerous benefits. Firstly, it thermally and mechanically isolates the camera from the optical bench, so that the sensor is distant from the infrared detector. Accordingly, heat generated by the camera is primarily dissipated by the thermal mass of the tip portion and does not propagate back to infrared detector 260. Secondly, locating the camera 300 near the distal end of the tip portion allows for the use of an inexpensive camera with a short working distance, thus requiring minimal optical components.

Figure 7:
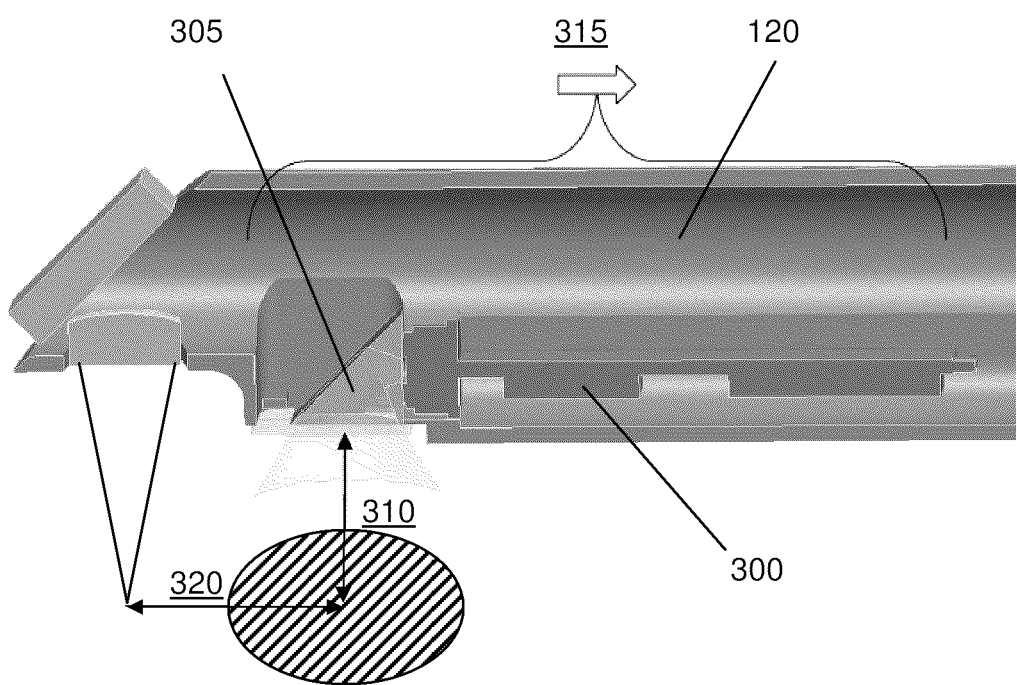
FIG. 7 illustrates the operation of a camera integrated into the tip portion of the handpiece.

FIGS. 4 and 7 illustrate an example embodiment in which the camera 300 used is a miniature CMOS imaging sensor with integrated NTSC video signal generation. The camera is effectively a "pinhole" type imaging system (with a small aperture and a fixed lens), thus providing large depth of field and viewing angle, without the added complexity and cost of imaging or beam redirecting optics such as mirrors and moving lenses. The very large depth of field accommodates the placement of the pinhole imaging system at wide range of distances relative to the tooth surface. The working distance 310 may be selected to be approximately 15-20 mm, providing an imaging area of approximately 10-20 mm in diameter. It is to be understood that the pinhole type camera described above is merely one example of a camera that may be employed, and that other miniature cameras may be substituted for the pinhole type camera.

As further shown in FIG. 7, the only optical component employed is a right angle prism 305, providing a robust and simple design. The prism 305 can be omitted by using a right angle camera module. In another embodiment, the camera may be placed at an increased axial distance (shown at 315) from the distal end of tip portion 120 to improve the operator direct line of sight of the area where PTR-LUM measurement is made, as shown in FIG. 7. The offset of the center of the imaging plane relative to the tip edge will increase accordingly. A suitable offset distance is approximately 20 mm.

In the example implementation shown in FIG. 7, the camera samples a spatial region that is spatially offset 320 from the location at which the laser is delivered. The spatial offset is beneficial in that the optical path of the camera does not interfere with the optical path of the PTR-LUM detection system. Although it is possible in alternative embodiments to image the tooth area directly during scanning, this would require filtering the light collected by the imaging system, which would be problematic as it would not render a true colour image of the imaged tooth due to the rejection of spectral components by the filter. Accordingly, the device may be operated such that the camera is not powered at the same time as the measurement of diagnostic data, thus avoiding the collection of stray laser light and also avoiding electrical and/or thermal crosstalk during the measurement process. Such a scheme is also beneficial as powering the camera only during use limits the generation of waste heat.

Figure 8:
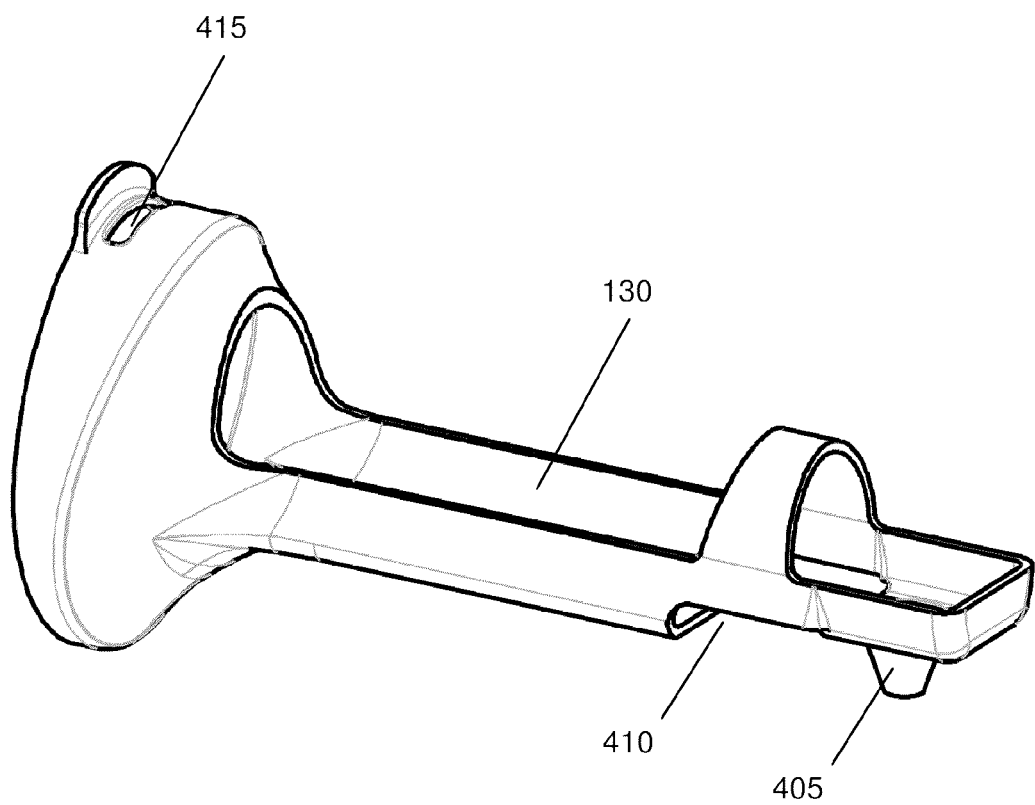
FIG. 8 shows a protective tip that is slidably received on the tip portion of the handpiece.

The tip portion 120 is may be fitted with an outer shell 130, shown in further detail in FIG. 8. The shell 130 includes cone section 405 with a hole provided therein for the delivery of the laser beam and the collection of photothermal and luminescent radiation. The length of the cone section may be selected to maintain a suitable working distance at the tip portion 120 relative to the focal length of the focusing element 240. Shell 130 also includes an aperture 410 providing optical access for the integrated camera 300. Shell 130 may be snap-fitted onto tip portion 120, for example, via feature 415 and a corresponding protruding feature in tip portion 120.

Shell 130 may be a disposable item that is used in combination with a sterile and transparent cover, such as a thin transparent material for protecting the handpiece and eliminating any cross-contamination among patients. The cover fits over the tip portion 120 of the hand piece so that it does not wrinkle or deform, thereby avoiding deflecting of signals or the distortion of camera images.

An example cover material is a transparent polymer layer that may be provided in the form of a bag, sheath or sock having a shape suitable for covering tip portion 120. The cover may be disposable. The cover is first placed over the tip portion, and the protective shell 130 is subsequently placed over the cover to secure it in place between the protective shell 130 and the tip portion 120. The protective shell 130 protects the cover against accidental breaching (puncturing/tearing) of the sterile barrier. The cover is partially or substantially transparent over a least a portion of the visible and near infrared spectrum (the portion where the laser light is delivered and the luminescence is generated) and the mid-infrared spectrum (where the photothermal radiation is generated). In one example, the transmissivity of the cover is at least 75% over the spectral region of interest. In another example, the transmissivity of the cover is at least 90% over the spectral region of interest.

In one example implementation, tip portion 120 may be provided in multiple sizes having a different working distances (or focal length) of focusing element 240. Different working distances can be useful depending upon the clinical situation. For example, smooth surfaces may be scanned with a different tip portion than the tip portion used to scan grooves on the biting surfaces of posterior teeth or interproximal (between teeth) spots. In such cases, a different shell 130 may also be provided for each different tip portion 120, so that the cone portion 405 of a given shell 130 accommodates a working distance for a corresponding tip portion 120. At times, one cone can be used with a universal length that would provide optimal signals from a wide range of tooth surfaces.

In one embodiment, a calibration device is further provided for use in calibrating the response of the handpiece. In the example implementation shown in FIG. 9, the calibration device 500 includes an internal axial bore 510 adapted to receive the outer surface of tip portion 120. Calibration device 500 includes a calibration reference material 520, such as a hydroxyapatite material suitable for the calibration of a photothermal and/or luminescence signal. A second calibration device housing a blackbody reference material such as glassy carbon may also be provided.

Figure 9:
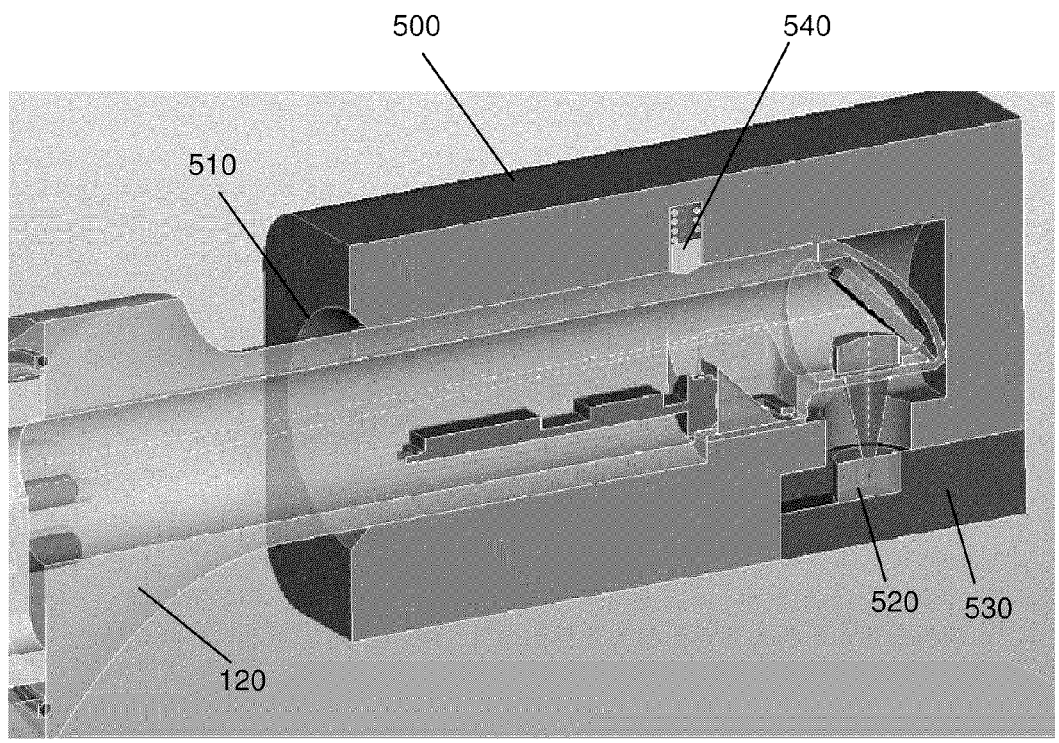
FIG. 9 shows a calibration device for use with the handpiece.

Referring again to the example device shown in FIG. 9, calibration reference material 520 is housed inside calibration device 500 such that when calibration device is secured on tip portion 120, calibration reference material 520 is located at or near a focal plane of focusing element 240, thereby facilitating the collection of a reference signal when a measurement is performed. Calibration device may be produced from machined plastic so it does not scratch the outer surface of tip portion 120 when in use, and is manufactured with sufficient tolerance for the correct alignment of tip to calibration reference material. In one example, calibration reference material 520 is housed in a separate portion 530 that is removably attached to the main body of the calibration reference device 500 for removal and/or replacement. In order to ensure the placement of calibration reference device 500 at a suitable position on the tip portion 120, positioning mechanism such as a spring plunger 540 which snaps on a small notch on the tip portion 120 or tension structure may be added to the main body.

Although the preceding embodiments relate to applications involving oral health diagnostics, it is to be understood that the scope of the present disclosure is not limited to dental uses and applications. The apparatus disclosed herein may be employed for a wide range of applications beyond dental detection, including other biological sensing and diagnostic applications, and non-destructive testing of various materials.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. An apparatus for detecting photothermal radiation from an object, said apparatus comprising:
   an elongate housing comprising:
   a handheld proximal portion comprising an inner recess; and
   a thermally conductive distal portion connected to said handheld proximal portion, said thermally conductive distal portion comprising a longitudinal inner bore and a distal aperture;
   a thermally conductive optical bench attached to said thermally conductive distal portion;
   a laser for producing a laser beam within said housing, said laser is mounted on said thermally conductive optical bench;
   a focusing element positioned to focus said laser beam through said distal aperture within said thermally conductive distal portion and onto a surface of said object, and to collect photothermal radiation generated within said object in response to said laser beam;
   a dichroic beamsplitter positioned within said housing to spatially separate said photothermal radiation from said laser beam; and
   an infrared detector for detecting said photothermal radiation,
   infrared detector is mounted on said thermally conductive optical bench; said thermally conductive optical bench is mechanically suspended within said inner recess of said proximal portion, without contacting said proximal portion, via attachment to said thermally conductive distal portion, such that heat generated by said laser and said infrared detector flows through said optical bench into said thermally conductive distal portion for passive heat sinking therefrom.

2. The apparatus according to claim 1 wherein a propagation axis of said laser beam within said housing is substantially collinear to a propagation axis of said photothermal radiation within said housing over a portion of a beam path of said laser beam.

3. The apparatus according to claim 1 wherein said laser beam comprises a wavelength suitable for generating luminescence radiation within said object, and wherein said focusing element is positioned to collect said luminescence radiation in addition to said photothermal radiation, said apparatus further comprising:
   an optical sampling element provided within said housing, wherein said optical sampling element is positioned to redirect sampled luminescence radiation;
   an optical filter positioned to transmit said sampled luminescence radiation and to reject scattered laser power; and
   a photodetector positioned to detecting said sampled luminescence radiation.

4. The apparatus according to claim 3 wherein said optical sampling element is a pick-off prism.

5. The apparatus according to claim 1 wherein said dichroic beamsplitter is positioned to reflect said laser beam and transmit said photothermal radiation.

6. The apparatus according to claim 5 wherein said dichroic beamsplitter is further configured to reflect luminescence radiation that is generated within said object and collected by said focusing element.

7. The apparatus according to claim 1 wherein said dichroic beamsplitter is positioned to transmit said laser beam and reflect said photothermal radiation.

8. The apparatus according to claim 7 wherein said dichroic beamsplitter is further configured to transmit luminescence radiation that is generated within said object and collected by said focusing element.

9. The apparatus according to claim 1 further comprising an optical absorbing element such that said photothermal radiation encounters said optical absorbing element prior to said infrared detector, and wherein said optical absorbing element is positioned to transmit said photothermal radiation and to absorb residual laser power.

10. The apparatus according to claim 9 wherein said optical absorbing element is further configured to absorb residual luminescence radiation that is generated within said object and collected by said focusing element.

11. The apparatus according to claim 9 wherein said optical absorbing element comprises a long pass filter.

12. The apparatus according to claim 11 wherein said long pass filter comprises a germanium window.

13. The apparatus according to claim 9 wherein said optical absorbing element is integrated with said dichroic beamsplitter.

14. The apparatus according to claim 1 wherein said distal portion of said housing further comprises a reflective element for externally redirecting said laser beam along a direction that is substantially orthogonal to a propagation axis of said laser beam within said housing.

15. The apparatus according to claim 1 wherein said distal portion of said housing comprises a camera for imaging said object.

16. The apparatus according to claim 15 wherein said aperture is a first aperture and wherein said camera is positioned to image said object through a second aperture that is adjacent to said first aperture.

17. The apparatus according to claim 15 wherein said camera is a pinhole type camera.

18. The apparatus according to claim 1 wherein said infrared detector is a (HgCdZn)Te detector.

19. The apparatus according to claim 1 wherein said laser is a semiconductor laser having a wavelength of approximately 660 nm.

20. The apparatus according to claim 1 further comprising a shell that is removably attachable to said distal portion of said housing, wherein said shell comprises an opening, and wherein said opening is aligned with said aperture when said shell is attached to said housing.

21. The apparatus according to claim 20 wherein said shell further comprises a conical projection, and wherein said opening is positioned at a distal end of said conical projection.

22. The apparatus according to claim 21 wherein a distance between said opening and said focusing element is approximately equal to a working distance of said focusing element.

23. The apparatus according to claim 20 further comprising a cover material provided between said shell and said distal portion of said housing, wherein said cover material is at least partially transparent to said laser beam and said photothermal radiation.

24. The apparatus according to claim 1 wherein said thermally conductive distal portion comprises aluminum.

25. The apparatus according to claim 1 further comprising a calibration device removably attachable to said distal portion of said housing, wherein said calibration device comprises a calibration reference material, wherein said calibration reference material is positioned within said calibration device such that said laser beam is directed onto said calibration reference material when said calibration device is attached to said housing.

26. The apparatus according to claim 25 wherein said calibration device comprises:
    an internal axial bore for receiving an outer surface of said distal portion of said housing; and
    an internal recess adjacent to said axial bore, said recess supporting said calibration reference material.

27. The apparatus according to claim 25 wherein said calibration reference material comprises one of hydroxyapatite and a blackbody reference material.

28. The apparatus according to claim 1 wherein said object is a tooth.

29. A system comprising:
    an elongate housing comprising:
    a handheld proximal portion comprising an inner recess; and
    a thermally conductive distal portion connected to said handheld proximal portion, said thermally conductive distal portion comprising a longitudinal inner bore and a distal aperture;
    a thermally conductive optical bench attached to said thermally conductive distal portion;
    a laser for producing a laser beam within said housing, said laser is mounted on said thermally conductive optical bench;
    a focusing element positioned to focus said laser beam through said distal aperture within said thermally conductive distal portion and onto a surface of said object, and to collect photothermal radiation generated within said object in response to said laser beam;
    a dichroic beamsplitter positioned within said housing to spatially separate said photothermal radiation from said laser beam; and
    an infrared detector for detecting said photothermal radiation,
    infrared detector is mounted on said thermally conductive optical bench; said thermally conductive optical bench is mechanically suspended within said inner recess of said proximal portion, without contacting said proximal portion, via attachment to said thermally conductive distal portion, such that heat generated by said laser and said infrared detector flows through said optical bench into said thermally conductive distal portion for passive heat sinking therefrom; and
    a control and processing unit connected to said apparatus, said control and processing unit is configured for providing power to said apparatus and for processing signals detected by said apparatus.

30. The system according to claim 29 wherein said control and processing unit comprises a phase-sensitive detection system for detecting a signal related to said photothermal radiation in response to a modulation of said laser beam.

31. The system according to claim 30 wherein said phase-sensitive detection system comprises a lock-in amplifier, wherein said lock-in amplifier is provided with a reference signal related to a phase of said modulation of said laser beam.

32. The system according to claim 29 wherein said control and processing unit further comprises a support for said elongate housing and a recess for protecting a distal end of said elongate housing when said elongate housing is resting in said support.

* * * * *